(12) United States Patent
Wall

(10) Patent No.: US 6,334,866 B1
(45) Date of Patent: Jan. 1, 2002

(54) STENT DEVICE FOR PERFORMING ENDOVASCULAR REPAIR OF ANEURYSMS

(76) Inventor: William H. Wall, 5139 Jimmy Carter Blvd., Norcross, GA (US) 30093

( * ) Notice: Subject to any disclaimer, the term of this patent is extended or adjusted under 35 U.S.C. 154(b) by 0 days.

(21) Appl. No.: 09/482,903

(22) Filed: Jan. 14, 2000

(51) Int. Cl.⁷ .................................................. A61F 2/06
(52) U.S. Cl. ..................... 623/1.12; 623/1.11; 623/1.16; 623/1.18
(58) Field of Search ................................ 623/1.11, 1.12, 623/1.13, 1.15, 1.16, 1.18, 1.32, 1.23

(56) References Cited

U.S. PATENT DOCUMENTS

| | | | |
|---|---|---|---|
| 4,969,896 A | * 11/1990 | Shors | 623/1 |
| 5,211,658 A | * 5/1993 | Clouse | 623/1 |
| 5,556,413 A | * 9/1996 | Lam | 606/198 |

* cited by examiner

Primary Examiner—David J. Isabella
Assistant Examiner—Urmi Chattopadhyay
(74) Attorney, Agent, or Firm—Eric P. Schellin

(57) ABSTRACT

A blood vessel wall-defining device for repairing an abdominal aneurysm. The device comprises a percutaneously-insertable structural frame extending between first and second ends having an unexpanded diameter which is smaller than the diameter of the blood vessel to permit the structural frame to be placed into the blood vessel. The structural frame being expansible to form a cylindrical structural skeleton having a slightly larger diameter than the blood vessel to facilitate the securing of the skeleton in position in the blood vessel. The skeleton has a sheath of a tubular fabric. The said structural frame has a plurality of spaced coiled stents prior to expansion which are uncoiled under the aegis of a balloon catheter and locked into position by ratchet means.

1 Claim, 3 Drawing Sheets

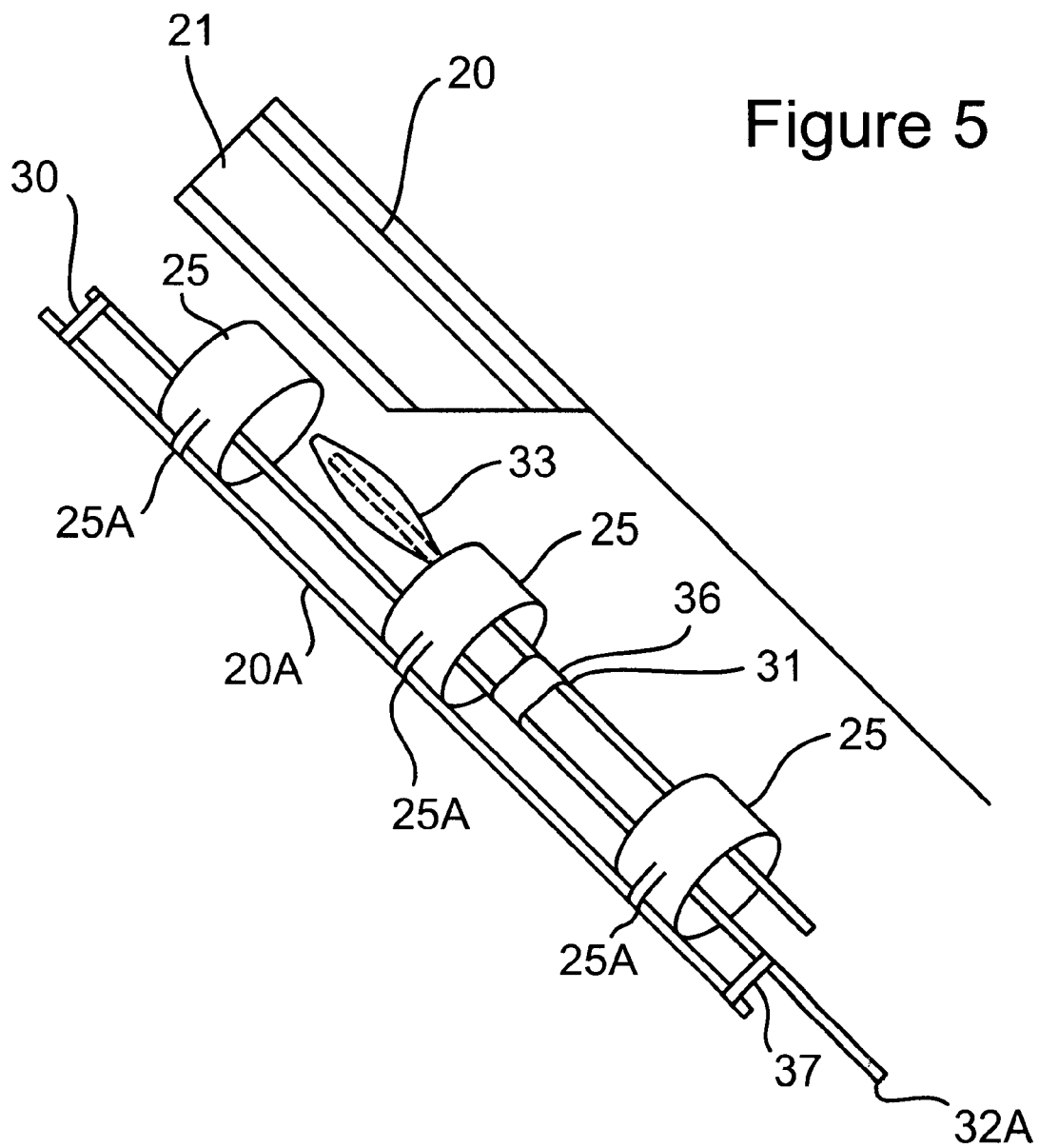

STENT DEVICE FOR PERFORMING ENDOVASCULAR REPAIR OF ANEURYSMS

BACKGROUND OF THE INVENTION

This application is by the same inventor, filed Jun. 21, 1996 under U.S. patent application Ser. No. 08/667,604, now U.S. Pat. No. 6,015,430 and is incorporated herein in its entirety.

This invention relates generally to blood vessel wall defining techniques and more specifically to a device and method capable of repairing aneurysms in large vessels employing percutaneous insertion.

Approximately 70% of the aneurysms reported in the United States each year are repaired by the conventional open surgical technique known as aneurysmectomy. However, the mortality rate associated with aneurysmectomy remains relatively high, 12.9% for elective surgery, 30–50% for emergency surgery after vascular rupture, and as high as 71% for patients over 70 years of age (Ruckley, In: The Cause and Management of Aneurysms, Greenhalgh R. M. et al. ed, W. B. Saunders, Philadelphia, p. 327–337, 1990; Lawrie et al, Surgery 85:483, 1979). Some of the factors involved in the high operative mortality rate are underlying coronary or cerebral atherosclerosis, severe obstructive pulmonary disease, and renal disease.

Another major disadvantage of aneurysmectomy is that, because of the nature of the operation, it can only be performed in medical facilities which have the sophisticated equipment necessary to perform major cardiovascular surgery. In cases where the prognosis for rupture is imminent, fatalities may occur because of insufficient time to perform diagnostic studies and/or transfer the patient to a major medical center where surgery can be performed. Therefore, there has been a long felt need for simpler, quicker and less traumatic techniques for repairing aneurysms.

Percutaneous techniques of blood vessel repair such as introducing vascular stents into arteries or veins have been suggested, and have had some significant applications, but known approaches have certain drawbacks and/or limitations and thus, have not found wide use with respect to large vessels, especially the abdominal aorta where a significant number of aneurysms occurs. Furthermore, it should also be borne in mind that the stents conventionally employed to open clogged arteries are quite different from an abdominal aneurysm stent, the latter often times has to deal with an aorta that is out of round cross-section wise because of the lesion area on the aorta.

Of late, the prior art workers have expended considerable efforts in the area of affecting repair of aneurysms of an abdominal aorta by specially fabricated stents. These efforts have led to the issuance of quite a few U.S. patents, namely:

U.S. Pat. No. 5,211,658 to Clouse
U.S. Pat. No. 5,360,443 to Barone et al
U.S. Pat. No. 5,387,235 to Chuter
U.S. Pat. No. 5,456,713 to Chuter
U.S. Pat. No. 5,522,880 to Barone et al
U.S. Pat. No. 5,562,726 to Chuter
U.S. Pat. No. 5,571,173 to Parodi
U.S. Pat. No. 5,676,697 to McDonald
U.S. Pat. No. 5,683,452 to Barone
U.S. Pat. No. 5,693,084 to Chuter
U.S. Pat. No. 5,755,777 to Chuter
U.S. Pat. No. 5,843,160 to Rhodes The subject matter of these patents are incorporated herein by reference.

The present invention builds on the prior work of the instant inventor W. Henry Wall as exemplified in U.S. Pat. Nos. 5,192,307, 5,824,038 and 5,843,163. The prior material is incorporated herein.

SUMMARY OF THE INVENTION

The present invention provides a blood vessel wall-defining device; and a method for insertion of the wall-defining device within a blood vessel of an animal, preferably a human patient, which has an abnormal widening, or aneurysm, along a section of the vessel wall. The insertion is particularly applicable to aneurysms in an aorta, especially in the abdominal aorta below the confluence with the renal arteries and above the bifurcation of the aorta into the common iliac arteries.

According to a first aspect of the invention a blood vessel wall-defining device for repairing an aneurysm comprises in combination, a percutaneously-insertable structural frame extending between first and second ends having an unexpanded diameter which is smaller than the diameter of the blood vessel to allow the structural frame to be percutaneously placed into the blood vessel, the structural frame being expansible to form a generally cylindrical structural skeleton having a slightly larger diameter than the blood vessel to facilitate the securing of the structural skeleton in position in the blood vessel.

The structural frame includes a plurality of flexible elongated rods which are equidistantly affixed to a sheath of fabric constructed of a thermoplastic material such as nylon. The sheath has a tubular configuration. Prior to percutaneous placement, the tubular cylinder is in undistended accordian-like folds to present a diminished diameter. The rods may be constructed of a bio-compatible metal or plastic.

Internally of the sheath are a series of displaced ring stents of a thermoplastic material or a bio compatible metal having a memory. These ring stents are coiled upon themselves to present a smaller diameter which upon uncoiling will provide an enlarged annular configuration. The coiled ring stents are retained in a coiled-up condition by an elongated pin which upon successful placement is retracted to permit uncoiling of the ring stents. The uncoiling of the ring stents provide the mechanical means to unfold the sheath or tube of fabric material to which the flexible metal or plastic rods are equidistantly attached.

In one embodiment, the ring stents, when constructed of a metal having a memory, would ordinarily recoil except that the end portions are provided with a ratchet locking means that retains the ring stent in its uncoiled position and therewith resistant to re-coiling. The ratchet means may be of a selected number whereby the stent ring means may be opened and progressively held at various uncoiled positions but cannot revert to a coiled position. The ratchet locking means is similar to the one disclosed in said parent application Ser. No. 08/667,604, filed on Jun. 21, 1996.

Due to the fact the device is relatively long the stent may under ordinary circumstances cover openings to branch arteries. In such a circumstance, it has been found useful to have certain portions of the device devoid of the tube of fabric material or sheath whereby blood may easily pass through the spaces between the rods of the device of the present invention.

As stated in another way, the ring stent provides a direct impingement on the flexible metal or plastic rods, i.e. without the presence of the fabric material or sheath.

It is contemplated that the device of the present invention may be positioned not only in the abdominal aorta but also in smaller branch arteries. In such a situation the diameter of the resulting device may describe a smaller diameter. The device can have a tube of fabric material or sheath throughout.

In another embodiment, the device for percutaneous insertion is carried by a known type of balloon catheter in a folded condition. The ring stents are in a coiled-up condition which upon successful placement of the device of the present invention the balloon is then inflated. The pressure of the balloon internally of the ring stent uncoils the stent which in turn impinges on the rod carrying fabric tube or sheath thereby unfolding the sheath and spacing the rods appropriately. The rods and sheath are detailed to abut and define the vessel wall of the artery.

BRIEF DESCRIPTION OF THE DRAWINGS

In the drawings:

FIG. 5 is a perspective of the device showing the retaining means for the individual ring stents.

DETAILED DESCRIPTION OF THE INVENTION

Figure 1:
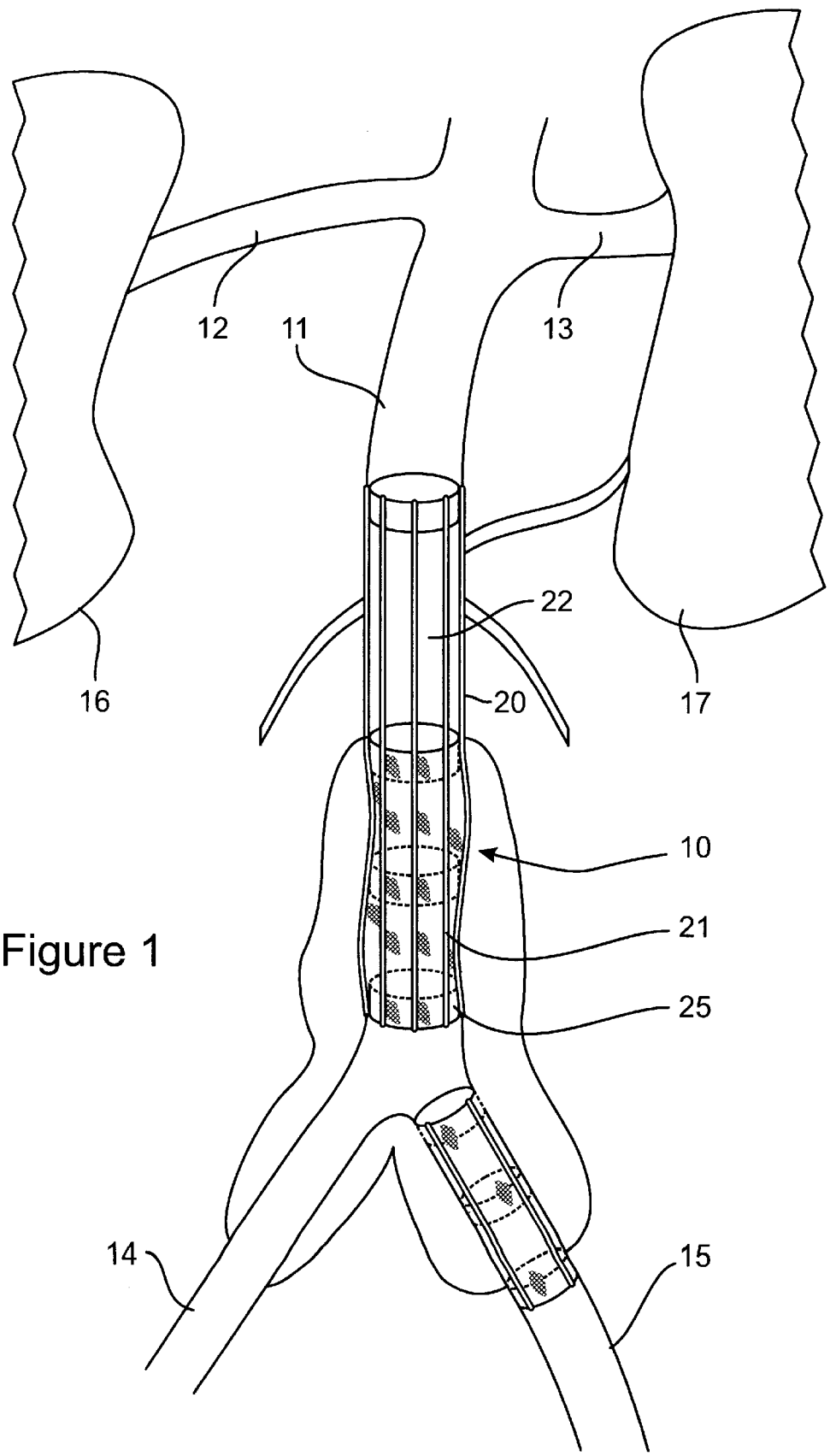
FIG. 1 is a perspective and diagrammatic view of the stent device of the present invention in place in an abdominal aorta.

Attention is now directed to FIG. 1 for a general view of the stent 10 of the present invention which is designed to be fitted into the abdominal aorta artery 11 in the area bordered at the top by the left renal artery 12 and the right renal artery 13. At the bottom, it is defined by the bifurcated left iliac artery 14 and the right iliac artery 15. The left and right renal arteries supply blood to the left kidney 16 and right kidney 17, respectively.

The abdominal aorta 11 may have an aneurysm or a ballooning out that may take various forms; suffice it to say that it is an outcropping of the wall of the aorta 11 resulting in a considerable weakening of the aorta which may lead to a rupture.

Such weakening will have little or no affect on the patient until it actually bursts and may not be known to exist. Sonograms can detect the aberration in wall disfiguration and outcropping. FIG. 1 shows an expanding aorta. Upon the bursting of the aorta's wall, the patient will bleed internally often to a point of death.

The stent shown in FIG. 1 is fabricated of a skeleton of elongated flexible metal rods 20 which are shown to be eight in number. It is contemplated that the number of rods may be greater or lesser in number, eight is preferred which are equidistant from each other when positioned.

The metal rods 20 are secured to a sheath 21 of fabric material which may elongatedly extend the entire length of the device or may terminate so that there is an open portion 22 while the rods 20 extend for an additional distance. The area unencumbered by the sheath provides fluid access between the rods so that branches off the abdominal aorta are supplied with blood.

Internally of the tube and rods is a series of ring stents 25. These ring stents are coiled prior to percutaneous insertion and are uncoiled under the aegis of a balloon carried by a catheter in one embodiment or, in another embodiment, automatically when a retaining pin is retracted from the ring stents and the latter are constructed of coiled metal having spring qualities.

Figure 2:
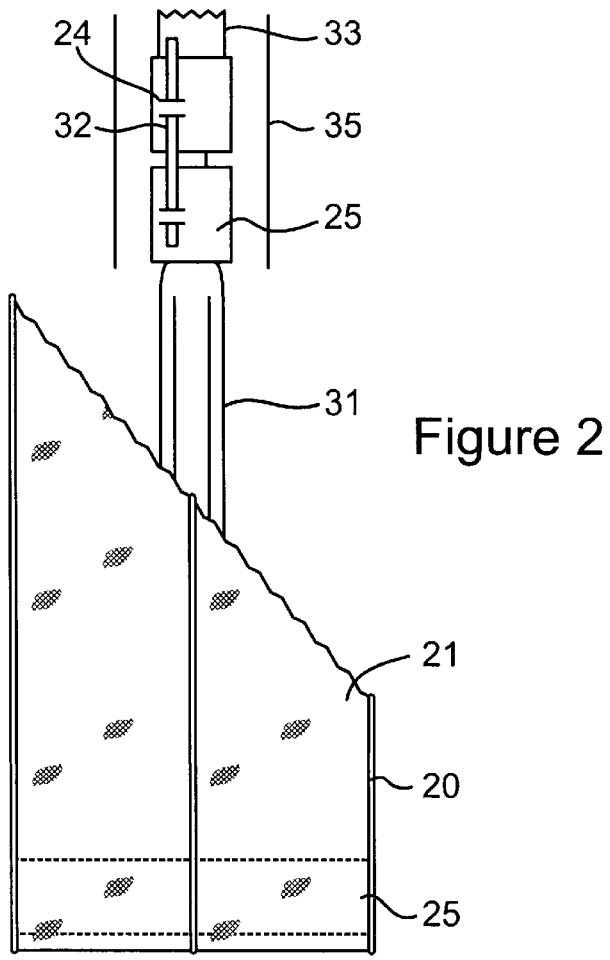
FIG. 2 is a fragmentary end view of the stent prepared for mounting.

FIG. 2 is a fragmentary view showing a diagrammatic view of the sheath 21 in an expanded condition with rods 20. The expansion is achieved by uncoiling ring stents 25 in either of the embodiments, both of which are shown in FIG. 2.

A catheter 31 is shown in a fragmentary fashion which is the carrying means for the implantation of the device. The FIG. 2 shows only a few of the ring stents 25 which are in a coiled position again. The ring stents are provided with a locking means which includes an elongated retractable pin 32 which is withdrawn from its locking position when the device 10 of the present invention is in place whereby the stent springs open, as stated, under its own accord when the stent is constructed of a material that has a spring memory whereby to assume an uncoiled configuration. When the ring stent, in the other embodiment, does not possess spring qualities, the unfurling must be assisted by means of a balloon in the catheter 31. To accomplish this the catheter 31 has an elongated balloon 33 which is conventional to a balloon catheter and is normally employed to open a blocked artery. In this instance it is detailed to assist to unfurl the ring stent 25 and thereby the stent 10 of the present invention by inflating the balloon 33 to a desired position.

Figure 3:
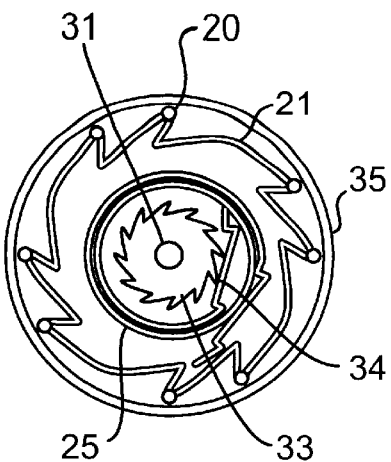
FIG. 3 is a cross-sectional view of the stent prior to being expanded.

FIG. 3 shows a cross-section of the stent 10 of the present invention in a conventional tubular member 35 prior to percutaneous disposition in aorta being afflicted by an aneurysm.

Note therein the folded-up sheath tube 21 and the coiled ring stent 25. The latter has a conventional plural ratchet locking means 34 for locking the ring stent 25 at selected positions in the progressively uncoiled position once the ring stent 25 has been expanded by balloon 33 supplied in a catheter 31.

Figure 4:
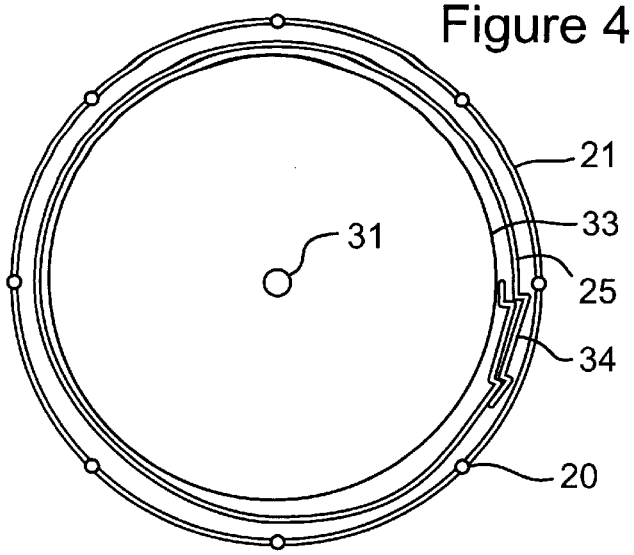
FIG. 4 is a cross-sectional view of the stent in an expanded condition.

In FIG. 4, one can view the cross-sectional view similar to that shown by FIG. 3 where the balloon 33 has uncoiled the ring stent 25 to its fullest position which is to the point of locking the ratchet lock or locks 34 as depicted. The ring stent in turn abuts outwardly radially against the sheath or fabric tube 21 with the attendant metal rods 20.

Attention is now directed to FIG. 5 which depicts another embodiment of the abdominal aortic stent system and shows the disposition thereof. A special single rod 20A of the rods 20 carries a plurality of ring stents 25 in a fixed spaced relationship. Each of the ring stents 25 has a compressible loop 25A through which the rod 20A is positioned. Securement is accomplished by compressing the loop 25A about the rod 20A. It is contemplated that a suitable adhesive may accomplish the securing of the said rod 20A to the ring stent 25. As in one of the foregoing embodiments the insertable balloon catheter 31 has an attachment 36 adapted and constructed to slide along an elongated slide rail 32A which has a distal attachment stop means 30 which is attached to the distal end portion of the rod 20A and, as stated, to which the ring stents 25 are attached. Another attachment means 37 is secured to the rod 20A to which the ring stents 25 are attached at its proximate end portion and radially to the slide rail 32A.

The catheter, surrounded by a conventional tubular member 35, is used to move the unfurled and undisposed stent 10 through the to-be treated aorta to a position opposite the aortic lesion. When properly positioned, the tubular member 35 is withdrawn. Then the slide pin 32 is withdrawn from the stent 10 and the lead ring stent 25. After all of the ring stents 25 have been permitted to uncoil and held in their respective places by retaining means, pin 32 is withdrawn from its attachment means 24 and removed with the catheter. It is contemplated that the catheter retracts from ring stent to ring stent.

In the case of employing ring stents that do not unfurl of their own accord, a balloon catheter is employed in a known manner. The balloon 33 is inflated to uncoil the lead ring stent 25, that is, as stated afore, when the stent is constructed of a material that wants to stay coiled and must be locked open to a position of abutment against the sheath 21 and in turn against the inner wall of the aorta. The lead ring stent remains locked open by the ratchets; the balloon 33 may be then deflated. The balloon catheter is withdrawn sliding along a guide rail 32A which acts as a guide for the balloon catheter so that the balloon can be reinflated at the next ring stent. In some embodiments it may be desirable to employ a balloon that has a suitable dimension that encompasses more than one ring stent 25 at a time.

The sheath 21 is attached to the rods 20 or ribs as discussed heretofore. Of course provision must be made for openings in the sheath 21 whereby the said loops 25A of the individual ring stents 25 may protrude therethrough.

One may construct various standardized sizes of the structural skeleton and thin walled flexible tubular member 35 for packaging into kits for use in the present invention.

The devices 10, as stated, may be preinstalled in the distal ends of respective catheters and may be injected by pusher devices similar to those employed to eject vena cava filters and the like. As stated, devices 10 are constrained by a tubular member 35, which may be a known delivery sleeve.

The distal ends of the rods 20 are rounded to hinder any undue abrasion against the aorta.

Various other modifications of the invention, within the spirit thereof and the scope of the claims, will occur to those skilled in the art.

What is claimed is:

1. A blood vessel wall defining device for repairing an aneurysm comprising in combination, a percutaneously-insertable structural longitudinal frame extending between a first end and a second end having an unexpanded diameter which is smaller than the diameter of said blood vessel for said structural frame to be percutaneously placed into said blood vessel, said structural frame being expandable to form a generally cylindrical structural skeleton having a slightly larger diameter than said blood vessel to facilitate the securing of said structural skeleton in position in said blood vessel, said structural frame including a plurality of longitudinal support rods, said support rods being attached to a tubular sheath for at least a portion thereof, a plurality of expandable ring stents longitudinally displaced internally of said tubular sheath, said ring stents prior to use are held in a coiled position by an elongated retractable pin having a coiled smaller deployment diameter prior to use and an expanded diameter in the uncoiled position.

* * * * *